(12) United States Patent
Lang et al.

(10) Patent No.: US 7,703,368 B2
(45) Date of Patent: Apr. 27, 2010

(54) KNIFE HOLDER FOR A MICROTOME HAVING A VIBRATING KNIFE

(75) Inventors: Anton Lang, Vienna (AT); Michael Zimmermann, Leopoldsdorf (AT)

(73) Assignee: Leica Mikrosysteme GmbH, Vienna (AT)

( * ) Notice: Subject to any disclaimer, the term of this patent is extended or adjusted under 35 U.S.C. 154(b) by 324 days.

(21) Appl. No.: 11/552,549

(22) Filed: Oct. 25, 2006

(65) Prior Publication Data

US 2007/0095188 A1 May 3, 2007

(30) Foreign Application Priority Data

Nov. 2, 2005 (DE) .................. 10 2005 052 228

(51) Int. Cl.
*B26D 7/26* (2006.01)
(52) U.S. Cl. .............. 83/698.11; 83/698.51; 83/698.61; 83/699.51; 83/699.61; 83/915.5
(58) Field of Classification Search ............. 83/698.11, 83/699.51, 915.5, 699.41, 698.71, 699.21, 83/699.61, 956, 701, 412, 856, 954, 699.11, 83/698.51, 698.61; 30/44, 68, 337, 335
See application file for complete search history.

(56) References Cited

U.S. PATENT DOCUMENTS

| 1,817,262 | A | * | 8/1931 | McGirr | ..................... 451/367 |
| 4,690,023 | A | | 9/1987 | Berleth et al. | |
| 4,700,600 | A | * | 10/1987 | Pickett | .................. 83/165 |
| 5,161,446 | A | * | 11/1992 | Holbl et al. | .................. 83/703 |
| 5,851,213 | A | * | 12/1998 | Berleth et al. | ............... 606/167 |
| 5,964,138 | A | | 10/1999 | Metzner et al. | |
| 6,871,572 | B1 | * | 3/2005 | Haussler et al. | ............... 83/542 |
| 7,013,987 | B2 | * | 3/2006 | Nock et al. | .................. 173/213 |

FOREIGN PATENT DOCUMENTS

DE        1878989 U1     9/1963
DE   202004007658 U1     8/2004

OTHER PUBLICATIONS

Microm International GMBH, Preisliste (Price List) 2003/2004, Jan. 2003, pp. 65-69, Germany.
The Vibratome Company, Vibratome Operating Instructions—Vibratome Series 3000 Plus—Tissue Sectioning System, Nov. 2001, U.S.A.

* cited by examiner

*Primary Examiner*—Boyer D Ashley
*Assistant Examiner*—Omar Flores-Sánchez
(74) *Attorney, Agent, or Firm*—Hodgson Russ LLP

(57) ABSTRACT

A knife holder for a microtome having a vibrating knife comprises a support element and a clamping element movable relative to the support element. The support element is embodied with a support surface for the knife, and the clamping element is embodied with a clamping surface. For clamping the knife, the support surface and clamping surface are settable at a distance of 0.1 to 1.5 from one another.

7 Claims, 4 Drawing Sheets

KNIFE HOLDER FOR A MICROTOME HAVING A VIBRATING KNIFE

CROSS-REFERENCE TO RELATED APPLICATIONS

The present application claims priority of German Patent Application No. 10 2005 052 228.9 filed Nov. 2, 2005, the entire disclosure of which is hereby incorporated herein by reference.

FIELD OF THE INVENTION

The present invention relates to a knife holder for a microtome having a vibrating knife. The invention relates in particular to a knife holder, the knife holder encompassing a support element and a clamping element movable relative to the support element. The support element is embodied with a support surface for the knife, and the clamping element is embodied with a clamping surface. The support surface and clamping surface are parallel to one another.

BACKGROUND OF THE INVENTION

The MICROM company discloses, on page 67 of its 2003/2004 price list, four different adapters for different blades. The user must buy a different adapter depending on the blade that is used. Misadjustment of the microtome can occur upon installation of a different knife holder.

The Vibratome company exhaustively describes, in its operating instructions for the Vibratome Series 3000 Plus Tissue Sectioning System, how double-edged razor blades must be broken in order to mount them in the same holder as the narrow-strip disposable blades (see page 9, left column, first paragraph).

A variety of knives are used for a microtome having a vibrating knife. These knives usually have different sizes and thicknesses. For example, a disposable razor blade is approximately 0.1 mm thick, and a sapphire knife approximately 1.2 mm thick. Because of the thinness of the razor blade, the clamping system must extend as close as possible to the knife cutting edge in order to stabilize it in the context of the cutting forces that occur. The expedient for these applications has hitherto been to change the knife holder. The disadvantages of this method are described in the existing art. A further disadvantage is that when razor blades having two oppositely located cutting edges are used, the razor blade must be broken in the middle.

SUMMARY OF THE INVENTION

It is therefore an object of the present invention to create a knife holder and knife assembly for a microtome having a vibrating knife, with which knives of different types can be retained in simple fashion; and with which the exchange of a knife is easy to carry out; and the risk of injury during a knife change is minimized by easy handling.

This object is achieved according to the present invention by a knife holder connected to a vibratory mechanism of the microtome, the knife holder including a support element having a support surface for a knife and a clamping element movable relative to the support element, the clamping element having a clamping surface parallel to the support surface, wherein the support surface and the clamping surface are settable at a distance from one another adaptable to a thickness of a knife to be held by the knife holder.

The invention has the advantage that for clamping the knife, the support surface and the clamping surface are settable at a distance of 0.1 to 1.5 mm from one another.

The support element is fixedly joined to the microtome, and the clamping element is embodied movably with respect to the support element.

An eccentric is provided which moves the clamping element along the support element and presses the clamping surface against the support surface, thus clamping the knife.

BRIEF DESCRIPTION OF THE DRAWINGS

Further advantages and advantageous embodiments of the invention may be inferred from the dependent claims and are the subject matter of the Figures below and their descriptions. Specifically:

DETAILED DESCRIPTION OF THE INVENTION

Figure 1:
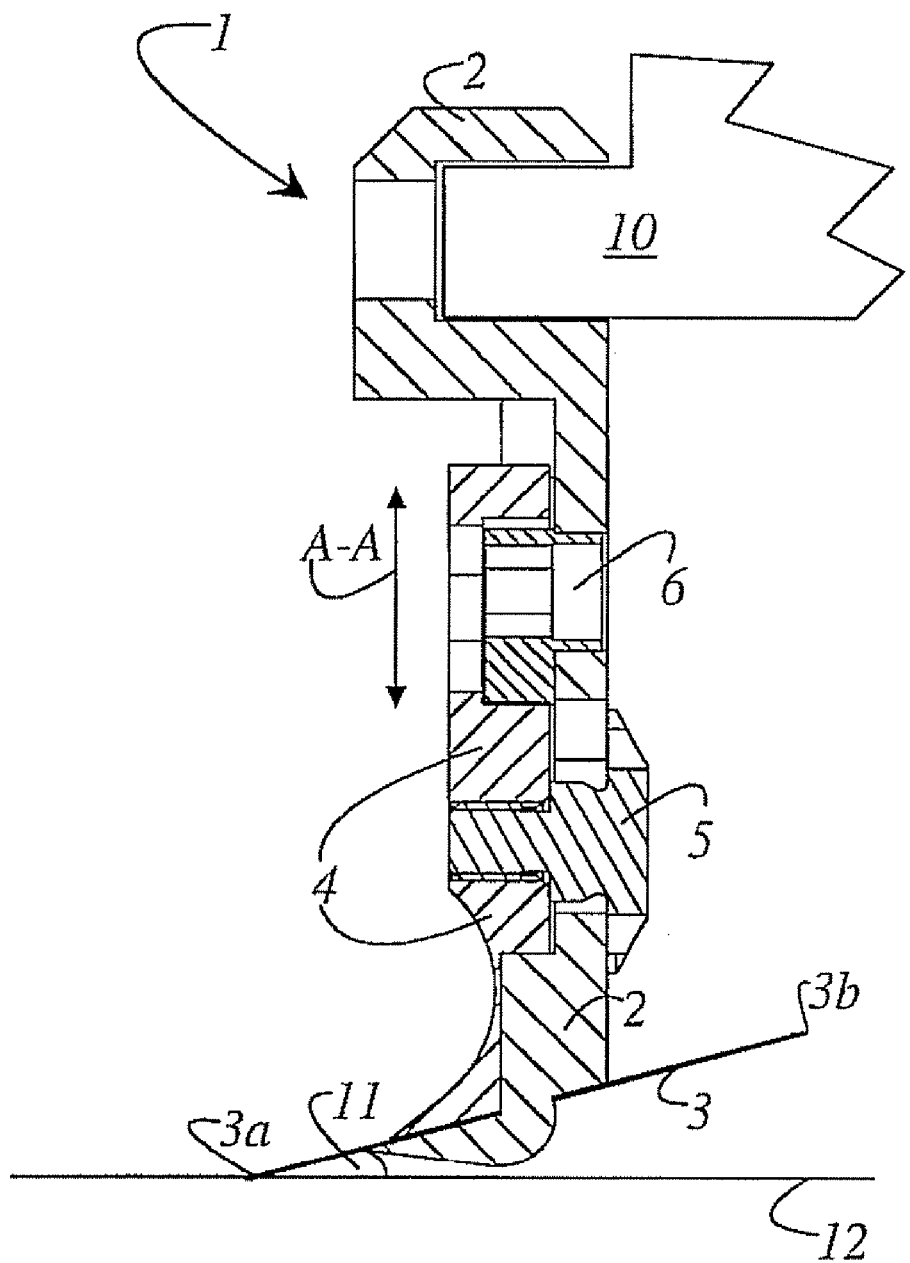
FIG. 1 is a sectioned view of the knife holder in which a knife having a cutting edge on both sides is retained.

FIG. 1 is a sectioned view of knife holder 1 in which a knife 3 having a cutting edge 3a and 3b on both sides is clamped. Knife holder 1 is made up of a support element 2 and a clamping element 4 movable relative to support element 2. Support element 2 is connected to vibratory mechanism 10 of the microtome. A screw 5 holds support element 2 and clamping element 4 together. Clamping element 4 is movable with respect to support element 2 in the direction of double arrow A-A. Knife 3 is mounted in knife holder 1 in such a way that it is inclined at an angle 11 with respect to the horizontal.

Clamping element 4 can be displaced parallel to support element 2 (in the direction of double arrow A-A). The displacement can be carried out with an eccentric 6.

Figure 2:
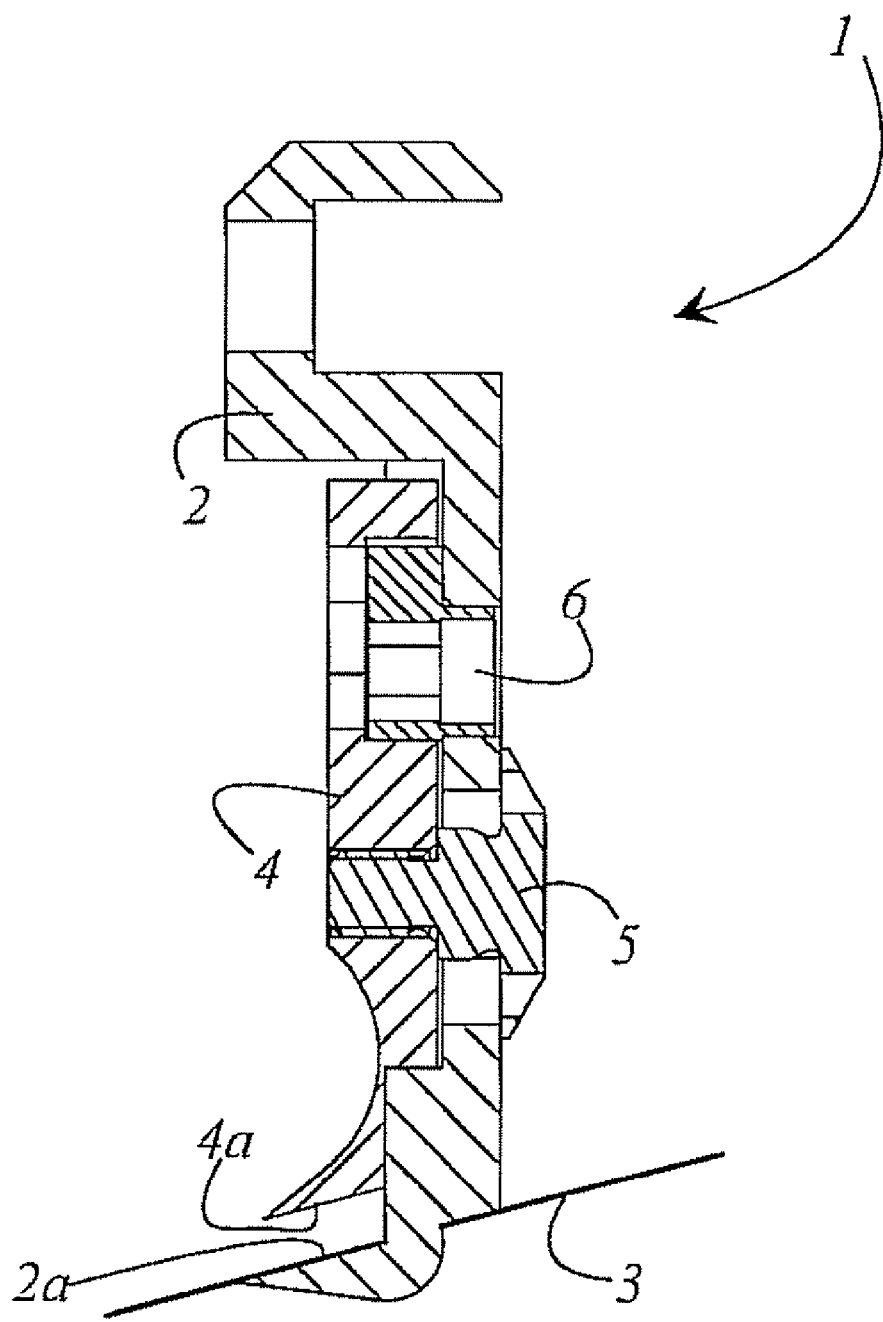
FIG. 2 is a sectioned view of the knife holder in which the clamping system for the knife having a cutting edge on both sides is open.

FIG. 2 is a sectioned view of knife holder 1 in which the clamping system for knife 3 having a cutting edge on both sides is open. As already mentioned, knife holder 1 encompasses support element 2 and clamping element 4 movable relative to support element 2. Support element 2 is embodied with a support surface 2a for knife 3, and clamping element 4 is embodied with a clamping surface 4a. Support surface 2a and clamping surface 4a are arranged in such a way that they are parallel to one another. In this arrangement, the knife thickness is uncritical. Eccentric 6 is designed in such a way that knife 3 can be clamped up to a thickness of approximately 1.5 mm. Screw 5 holds support element 2 and clamping element 4 together, and guarantees a parallel displacement when eccentric 6 is rotated by means of a tool (not depicted). In order to clamp knife 3, support surface 2a and clamping surface 4a can be set at a distance of 0.1 to 1.5 mm from one another. In the open position (shown in FIG. 2) of knife holder 1, knives 3 having two blades, e.g. razor blades, can be slid over a receptacle 32 (see FIG. 3) of support element 2. The knives used have, as a rule, a thickness of 0.1 to 1.5 mm; those skilled in the art will recognize that alternative means for modifying the distance between support surface 2a and clamping surface 4a, such as threaded spindle drives, levers, ratchets and the like, may be used instead of an eccentric.

Figure 3:
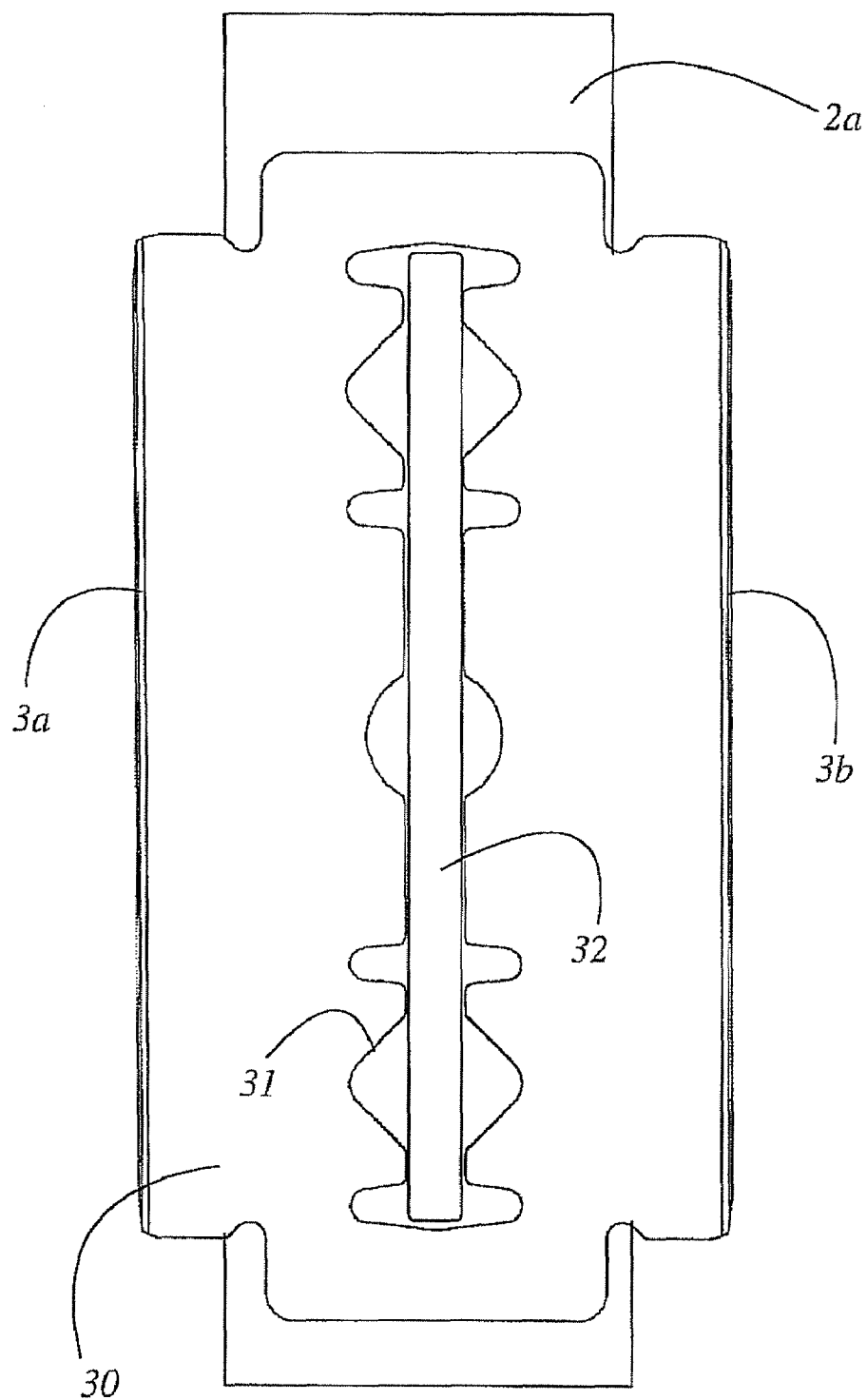
FIG. 3 is a plan view of a razor blade such as the one used in the context of the present invention.

FIG. 3 is a plan view of a razor blade 30 such as the one used in the context of the present invention. The razor blade is embodied with a cutting edge 3a and 3b on both sides. Razor blades 30 likewise possess a central opening 31 that serves for mounting or installation of razor blade 30 in a tool. In the case of the present invention, support element 2 is embodied with receptacle 32 that serves to immobilize razor blade 30.

Figure 4:
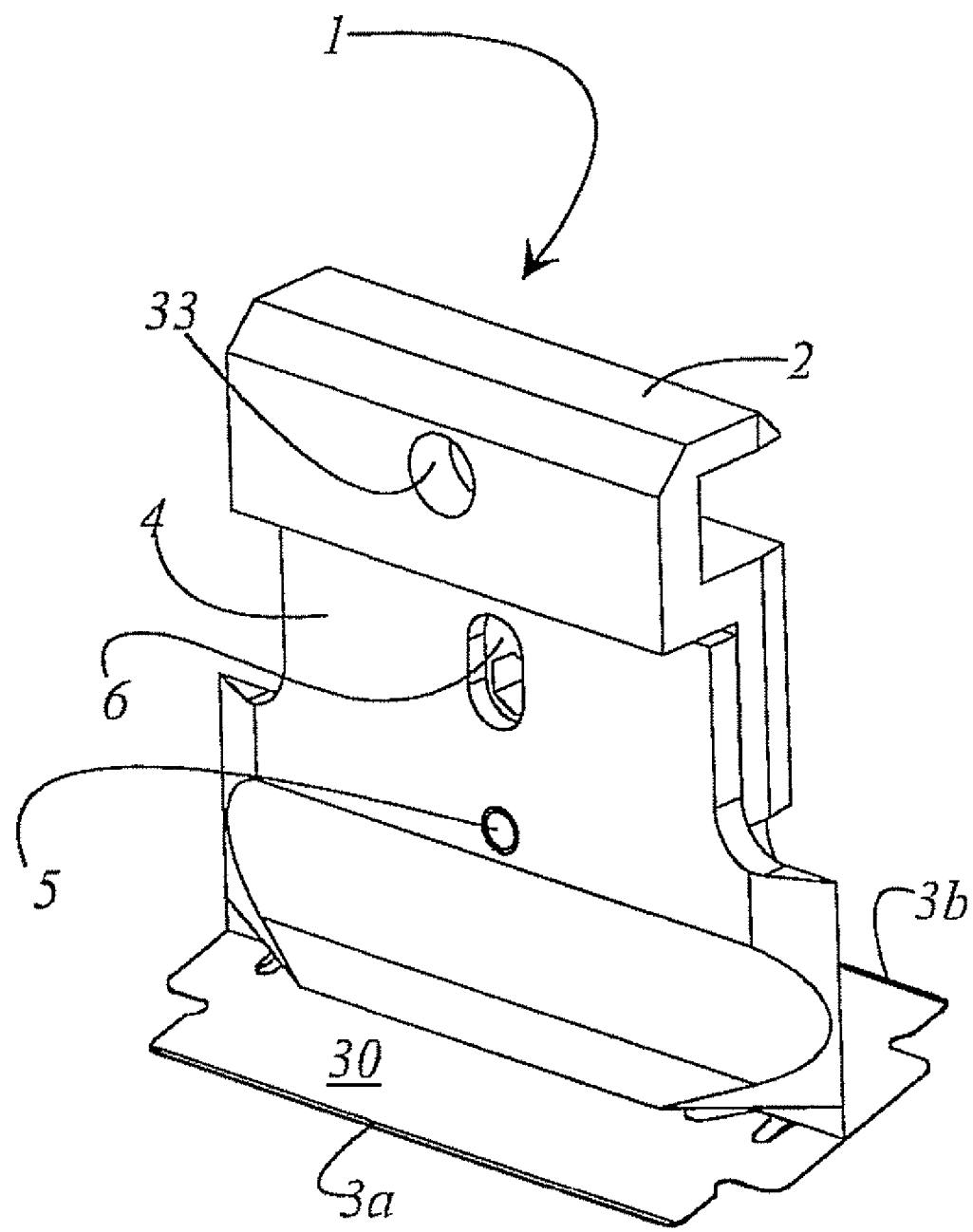
FIG. 4 is a perspective view of the knife holder, a razor blade being clamped.

FIG. 4 is a three-dimensional view of the complete knife holder 1. A razor blade 30 is retained and clamped in knife holder 1.

What is claimed is:

1. A knife assembly for a microtome comprising:
a vibratory mechanism (10); and
a knife holder connected to the vibratory mechanism, the knife holder including a support element (2) having a support surface (2a) for a knife and a clamping element (4) movable relative to the support element (2), the clamping element (4) having a clamping surface (4a) parallel to the support surface (2a), wherein the support surface (2a) and the clamping surface (4a) are settable at a distance from one another adaptable to a thickness of a knife to be held by the knife holder and the support surface (2a) and the clamping surface remain parallel to one another as the distance between the support surface and the clamping surface (4a) is adapted;
wherein the support element (2) of the knife holder is fixedly joined to the vibratory mechanism, and the clamping element is movable along the support element, wherein the knife holder further includes an eccentric (6) rotatably mounted on the support element and arranged to engage the clamping element for moving the clamping element (4) along the support element in a clamping direction to clamp a knife between the support surface and the clamping surface, and a fastener (5) extending perpendicular to the clamping direction and arranged to hold the clamping element (4) and the support element (2) together, wherein the fastener (5) and the eccentric (6) are arranged between the vibratory mechanism (10) and the support surface (2a).

2. The knife assembly (1) according to claim 1, wherein the support surface and the clamping surface are settable at a distance from one another ranging from 0.1 to 1.5 mm.

3. The knife assembly according to claim 1, further comprising a knife clamped between the support surface and the clamping surface.

4. The knife assembly according to claim 3, wherein the knife includes only a single cutting edge on one side thereof.

5. The knife assembly according to claim 3, wherein the knife includes a pair of cutting edges arranged on opposite sides of the knife, and both of the pair of cutting edges are free from engagement with the knife holder.

6. The knife assembly according to claim 5, wherein the knife is a razor blade (30) having an opening (31) between the pair of cutting edges (3a, 3b).

7. The knife assembly according to claim 6, wherein the support surface (2a) has a receptacle (32) sized for receipt through the opening (31) of the razor blade (30).

* * * * *